United States Patent
Piazza et al.

(10) Patent No.: US 10,259,839 B2
(45) Date of Patent: Apr. 16, 2019

(54) 3-(4'-SUBSTITUTED)-BENZYL-ETHER DERIVATIVES OF PREGNENOLONE

(71) Applicants: INSERM (Institut National de la Sante et de la Recherche Medicale), Paris (FR); SC BELENOS, Bordeaux (FR); Universite de Bordeaux, Bordeaux (FR)

(72) Inventors: Pier Vincenzo Piazza, Bordeaux (FR); Monique Vallee, Bordeaux (FR); Francois-Xavier Felpin, Nantes (FR); Jean-Michel Revest, Bordeaux (FR); Sandy Fabre, Cenon (FR)

(73) Assignees: INSERM (INSTITUT NATIONAL DE LA SANTE ET DE LA RECHERCHE MEDICALE), Paris (FR); SC BELENOS, Bordeaux (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 14/443,778

(22) PCT Filed: Nov. 27, 2013

(86) PCT No.: PCT/EP2013/074886
§ 371 (c)(1),
(2) Date: May 19, 2015

(87) PCT Pub. No.: WO2014/083068
PCT Pub. Date: Jun. 5, 2014

(65) Prior Publication Data
US 2015/0284423 A1    Oct. 8, 2015

(30) Foreign Application Priority Data
Nov. 28, 2012    (EP) .................................... 12194704

(51) Int. Cl.
*A61K 31/57*    (2006.01)
*C07J 7/00*    (2006.01)
*C07J 41/00*    (2006.01)

(52) U.S. Cl.
CPC ............. *C07J 7/0045* (2013.01); *C07J 7/002* (2013.01); *C07J 41/005* (2013.01); *C07J 41/0094* (2013.01)

(58) Field of Classification Search
CPC ........ C07J 7/002; C07J 7/0045; C07J 41/005; C07J 41/0094; A61K 31/57
USPC .................. 552/592, 606; 514/182
See application file for complete search history.

(56) References Cited

U.S. PATENT DOCUMENTS

| | | |
|---|---|---|
| 3,084,174 A | 4/1963 | Patchett et al. |
| 3,169,133 A | 2/1965 | Ayer |
| 3,244,696 A | 4/1966 | Mainil |
| 3,351,639 A | 11/1967 | Allen et al. |
| 3,361,744 A | 1/1968 | Schaub et al. |
| 4,622,317 A | 11/1986 | Hsia et al. |
| 4,628,052 A | 12/1986 | Peat |
| 4,933,157 A | 6/1990 | Counsell et al. |
| 5,175,154 A | 12/1992 | Schwartz et al. |
| 5,226,943 A | 7/1993 | Hulshof |
| 5,232,917 A | 8/1993 | Bolger et al. |
| 5,506,220 A | 4/1996 | Schwadrohn |
| 5,763,431 A | 6/1998 | Jackson |
| 5,968,918 A | 10/1999 | Kanda |
| 6,455,516 B1 | 9/2002 | Backstrom et al. |
| 7,960,553 B1 | 6/2011 | Dudley |
| 2003/0125311 A1 | 7/2003 | Baulieu et al. |
| 2006/0199790 A1 | 9/2006 | Baulieu et al. |
| 2008/0015171 A1 | 1/2008 | Smith |
| 2008/0171728 A1 | 7/2008 | Bridges |
| 2009/0143347 A1 | 6/2009 | Baulieu et al. |
| 2009/0203658 A1 | 8/2009 | Marx |

FOREIGN PATENT DOCUMENTS

| | | |
|---|---|---|
| DE | 972443 | 10/1959 |
| DE | 1166189 | 3/1964 |

(Continued)

OTHER PUBLICATIONS

Chen et al., "Intradermal pregnenolone sulfate attenuates capsaicin-induced nociception in rats," Biochem. Biophys. Res. Commun., 349(2):626-633 (2006) Abstract only.

(Continued)

*Primary Examiner* — Barbara P Badio
(74) *Attorney, Agent, or Firm* — McDermott Will & Emery LLP

(57) ABSTRACT

The invention relates to a compound of Formula (I), or a pharmaceutically acceptable salt thereof: wherein R1 is C1-8 alkyl, C1-8 alkoxy, CN, $NO_2$, amino, COOH, $COOCH_3$, OH, $N_3$, or halogen and R2 is H, OH, C1-8 alkyl, C1-8 alkoxy, C2-C6 alkenyl, halogen, Bn-O—, Bn- optionally substituted, or Ph- optionally substituted.

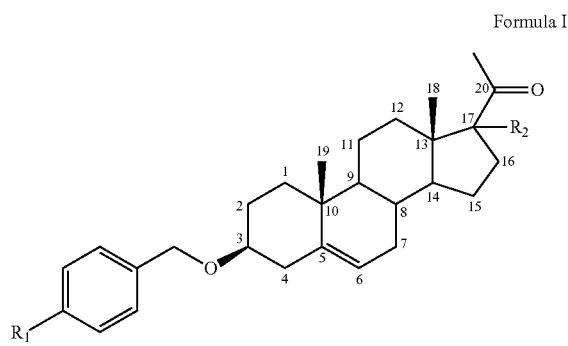

Formula I

4 Claims, No Drawings

(56) References Cited

FOREIGN PATENT DOCUMENTS

| | | |
|---|---|---|
| EP | 1020191 | 7/2000 |
| FR | 2850023 | 7/2004 |
| KR | 20050023998 | 3/2005 |
| WO | 1998014194 A1 | 4/1998 |
| WO | 9833506 | 8/1998 |
| WO | 9837897 | 9/1998 |
| WO | 2001022959 | 4/2001 |
| WO | 2002036128 | 5/2002 |
| WO | 2002072003 | 9/2002 |
| WO | 2002089814 | 11/2002 |
| WO | 2003045362 | 6/2003 |
| WO | 2003059357 | 7/2003 |
| WO | 2006002907 | 1/2006 |
| WO | 20060307016 | 4/2006 |
| WO | 2006077209 | 7/2006 |
| WO | 2010107922 | 9/2010 |
| WO | 2010136000 | 12/2010 |
| WO | 2012/160006 | 11/2012 |

OTHER PUBLICATIONS

International Search Report for International Application No. PCT/EP2013/074886 dated Feb. 6, 2014.
Autenrieth et al., "Synthesis of 3- and 6-substituted steroidal heterocycles as potential anticancer agents," Chimica Therapeutica, Nov.-Dec. 1981-16, No. 6, pp. 525-528.
Banday et al., "Studies on novel D-ring substituted steroidal pyrazolines as potential anticancer agents," www.elsevier.com/locate/steroids, 2010, 5 pages.
Benedetti et al., "Improved Procedure for the Cleavage of Alkyl and Benzyl Ethers with Zinc Iodide," J. Chem Research, 1990, 2 pages.
Hodosan et al., "A new partial synthesis of Holaphyllamine", Sep. 15, 1968, 2 pages.
Li et al., "Synthesis of 3β-hydroxypregn-5-en-20-one A and B ring derivatives and studies on their structure-activity relationships," Yaoxue Xuebao, vol. 17, Issue 4, Journal 1982, pp. 265-74.
Luo et al., "Study on the synthesis of 3β,21-dihydroxypregn-5-en-20-one-21-methyl ether," Huaxue Shiji, vol. 30, Issue 9, Journal 2008, pp. 702-704, Abstract.
Pillai et al., "Multiple structural features of steroids mediate subtype-selective effects on human α4β3σ GABAA receptors," Biochemical Pharmacology 68 (2004) 819-831.
Deghenghi et al., "New synthesis and structure activity relationship in the 17-alkylated progesterone series," May 1963, 4 pages.
Vitali et al., "Alkylation of steroids during Claisen rearrangement of allyl and preopargyl enolethers. IV. Transposition of 20-oxo steroid enol ethers," 1967, 2 pages.
Roberts, "Pregnenolone—from Selye to Alzheimer and a model of pregnenolone sulfate binding site on the GABAA receptor," Biochemical Pharmacology, vol. 49, No. 1, pp. 1-16, 1995.
Allen et al., "New progestational Agents, Nonclassical 17-Alkylpregnene structures," J. Med. Chem., 7:684-686, 1964.
Anaraki et al., "Modulation by female sex hormones of the cannabinoid-induced catalepsy and analgesia in ovariectomized mice," European Journal of Pharmacology 586, 2008, 189-196.
Rodriguez De Fonseca et al., "Cannabinoid receptors in rat brain areas: sexual differences, fluctuations during estrous cycle and changes after gonadectomy and sex steroid replacement," Life Sciences, vol. 54, pp. 159-170.
Chianese et al., "Desulfohaplosamate, a new phosphate-containing steroid from *Dasychalina* sp., is a selective cannabinoid CB2 receptor ligand," Steroids, 76(10):998-1002, 2011.
Shi et al., "OSW Saponins: Facile Synthesis toward a New Type of Structures with Potent Antitumor Activities", J Org Chem, 2007, 70, 10354-10367.
Pozzie et al., "A Mild Radical Procedure for the Reduction of B-Alkylcatecholboranes to Alkanes", J Am Chem Soc, 2005, 127, 14204-14205.
Veiga, et al. "Neuroprotection by the Steroids Pregnenolone and Dehydroepiandrosterone is Mediated by the Enzyme Aromatase", Neuroprotection by Neuroactive Steroids, 2002, 398-406.

3-(4'-SUBSTITUTED)-BENZYL-ETHER DERIVATIVES OF PREGNENOLONE

The present application is filed pursuant to 35 U.S.C. 371 as a U.S. National Phase application of International Patent Application No PCT/EP2013/074886, which was filed Nov. 27, 2013, claiming the benefit of priority to European Patent Application No. 13795536.5, which was filed Nov. 28, 2012. The entire text of the aforementioned applications is incorporated herein by reference in its entirety.

FIELD OF THE INVENTION

The present invention relates to synthetic neuroactive steroids and more particularly to synthetic Pregnenolone derivatives and their use in a method for treatment of the human or animal body.

BACKGROUND OF THE INVENTION

Various steroids synthesized in the adrenal glands and gonads are capable of modulating neuron excitability in the CNS. For these compounds the term "neuroactive steroids" has been coined (Majewska et al., 1986), or "neurosteroids" for those that the brain can synthesize de novo (Baulieu, 1991).

Steroid hormones have long been recognized to have sedative, anesthetic and anti-seizure properties in animals and humans (Aird, 1944; Aird and Gordan, 1951; Gyermek et al., 1967; Green et al., 1978). Studies during the past two decades have uncovered that progesterone and deoxycorticosterone serve as precursors for the endogenous neurosteroids allopregnanolone (5α-pregnane-3α-ol-20-one) and THDOC (5α-pregnane-3α,21-diol-20-one), respectively (Reddy, 2003; 2009a). Testosterone-derived androgens such as androstanediol (5α-androstane-3α,17β-diol) and estradiol can be considered as neurosteroids (Reddy, 2008). Generally, the acute effects of neurosteroids are not related to interactions with classical steroid hormone receptors that regulate gene transcription. Moreover, neurosteroids are not themselves active at intracellular steroid receptors. They modulate brain excitability primarily by interaction with neuronal membrane receptors and ion channels, principally GABA-A receptors (Lambert et al., 2003; Reddy, 2003; Akk et al., 2009).

In addition to endogenous steroids such as pregnenolone sulfate, DHEA-S, estradiol, or progesterone for which neuroactive properties have been described (Paul and Purdy, 1992; Rupprecht, 1997), synthetic steroids have been developed recently that share their endogenous counterparts' characteristic of modulating a variety of G-protein-coupled receptors and ligand-gated ion channels (Gasior et al., 1999).

Some synthetic neurosteroids that show better pharmacokinetics and efficacy are evaluated for sedative and anxiolytic (minaxolone), anesthetic (alphaxolone) and antiepileptic (ganaxolone) effects.

However, the diverse in vivo actions of neuroactive steroids depend on the lack of specificity of natural and synthetic steroids that do not bind uniquely to one neurotransmitter receptor but on several of them. The metabolism of neuroactive steroids with metabolites that exhibit different pharmacological profiles compared to their precursors is also responsible for the variety of effects of a single steroid. As yet, no derivatives of naturally occurring or synthetic steroids have been developed that show exclusive receptor specificity or avoid side effects due to it metabolization.

SUMMARY OF THE INVENTION

Among the naturally occurring steroid, studies that demonstrate an in vivo effect by pregnenolone are very few but they suggest a beneficial role for this steroid. It was shown that pregnenolone administration decreased the formation of gliotic tissue following a penetrating lesion in rat cerebral cortex and hippocampus (Garcia-Estrada et al., 1999). Pregnenolone was showed to protect against toxicity induced by glutamate and the protein beta amyloid in hippocampal cells line (HT-22) cultures (Gursoy et al., 2001). Furthermore, pregnenolone has also been suggested to enhance memory performance (Mathis et al., 1994). However, these effects of pregnenolone have been classically attributed to the downstream metabolites of pregnenolone, that in itself is considered the inactive precursor of downstream active steroids. Thus, pregnenolone has not effects on the principal targets of neuroactive steroids that are the GABA and Excitatory aminoacid receptors.

Recently, the inventors have shown that pregnenolone acts as an inhibitor of the human CB1 receptor with a pharmacological profile different from orthosteric antagonist and from other neuroactive steroids, which indicates that pregnenolone has less unspecific and undesiderable effects than orthosteric antagonists of the CB1 and other neuroactive steroids (patent application PCT/EP2012/059310 published under WO2012/160006; Vallée et al., 2013).

Given that pregnenolone is the first step of steroid synthesis in the brain and other organ, pregnenolone is not considered as a good target to derive synthetic neuroactive steroids from.

Indeed, such pregnenolone derivatives present high risk to be metabolised. The generated metabolites could exhibit different pharmacological profiles compared to their precursors and exert side effects.

The inventors have found that molecules derived from pregnenolone that contain a 3-benzyloxy function (substituted or not) cannot be converted into metabolites endowed with progestative, androgenic, estrogenic, and glucocorticoid activity. Therefore, using these pregnenolone derivatives that are not or not substantially converted into pregnenolone metabolites avoids side effects.

Thus, the present invention relates to a compound of Formula I or a pharmaceutically acceptable salt thereof, Formula I

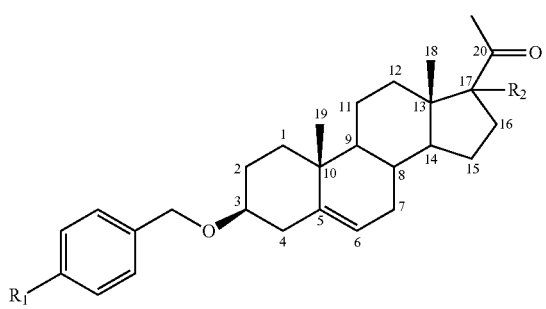

wherein:
R1 is:
C1-8 alkyl,
C1-8 alkoxy,
CN,

NO$_2$,
amino,
COOH,
COOCH$_3$
OH,
N$_3$,
or
halogen
and
R2 is:
H,
OH,
C1-8 alkyl,
C1-8 alkoxy,
C2-C6 alkenyl,
halogen,
Bn-O—
Bn- optionally substituted with C1-8 alkyl, C1-8 alkoxy, CN, NO$_2$, amino, COOH or halogen or
Ph- optionally substituted with C1-8 alkyl, C1-8 alkoxy, CN, NO$_2$, amino, COOH or halogen.

DETAILED DESCRIPTION OF THE INVENTION

Definitions

The term "Agonist" refers to a compound that enhances the activity of another compound or receptor site.

The terms "Antagonist" and "Inhibitor" refer to a compound that diminishes or prevents the activity of another compound at a receptor site and more generally refer to a compound that diminishes or prevents the activation and/or the activity of a receptor.

The terms "Treatment or treating" refer to both therapeutic treatment and prophylactic or preventive measures, wherein the object is to prevent or slow down the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

As used herein, the term "subject" denotes a mammal, such as a rodent, a feline, a canine, and a primate. Preferably, a subject according to the invention is a human.

A "therapeutically effective amount" is intended for a minimal amount of active agent which is necessary to impart therapeutic or a preventive benefit to a subject. For example, a "therapeutically effective amount" to a mammal is such an amount which induces, ameliorates or otherwise causes an improvement in the pathological-symptoms, disease progression or physiological conditions associated with or resistance to succumbing to a disorder.

"Alkyl" means monovalent linear or branched saturated hydrocarbon moiety, consisting solely of carbon and hydrogen atoms. C1-8 alkyl means a linear or branched alkyl having from one to eight carbon atoms.

"Alkoxy" means a moiety of the formula —OR, wherein R is an alkyl moiety as defined herein.

The term "alkenyl" used herein describes an unsaturated, linear or branched aliphatic hydrocarbon having at least one carbon-carbon double bond. "C2-6 alkenyl" denotes a straight- or branched-chain of 2 to 6 carbon atoms with at least one double bond.

The term "halogen", alone or in combination with other groups, denotes chloro (Cl), iodo (I), fluoro (F) and bromo (Br).

The term "cyano", alone or in combination with other groups, denotes the group —CN.

The term "hydroxyl", alone or in combination with other groups, denotes the group —OH.

The term "nitro", alone or in combination with other groups, denotes the group —NO$_2$.

The term "carboxyl", alone or in combination with other groups, denotes the group —COOH.

"Amino" means a moiety of the formula —NRR' wherein R and R' each independently is hydrogen, or alkyl as defined herein.

The abbreviation Bn refers to a benzyl group.

The abbreviation Ph refers to a phenyl group.

The term "pharmaceutically acceptable salts" refers to salts that are suitable for use in contact with the tissues of humans and animals without undue toxicity, irritation, allergic response, and the like. Examples of suitable salts include salts of alkali metals such as potassium, sodium, lithium, salts of alkaline earth metals such as calcium, magnesium and acid addition salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, hemisuccinic acid, tartaric acid, methane-sulfonic acid, p-toluenesulphonic acid, trifluoro acetic acid and the like.

Substituents above the plane of the molecule are shown as a solid line (—) and are described as β; those below the plane are shown by a broken line (⋯) and are described as α.

Compounds of the Invention

General Formula:

The invention relates to compounds of Formula I or pharmaceutically acceptable salts thereof:

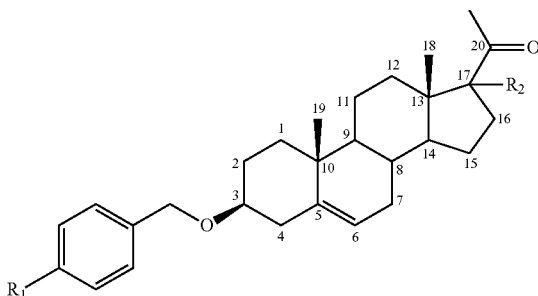

Formula I wherein:
R1 is:
C1-8 alkyl,
C1-8 alkoxy,
CN,
NO$_2$,
amino,
COOH,
COOCH$_3$
OH,
N$_3$,
or
halogen
and R2 is:
H,
OH,
C1-8 alkyl,
C1-8 alkoxy,
C2-C6 alkenyl,
halogen,
Bn-O—
Bn- optionally substituted with C1-8 alkyl, C1-8 alkoxy, CN, $NO_2$, amino, COOH or halogen
or
Ph- optionally substituted with C1-8 alkyl, C1-8 alkoxy, CN, $NO_2$, amino, COOH or halogen.

In one preferred embodiment, R2 is in α position.
In this embodiment, the compounds of the invention have the Formula II:

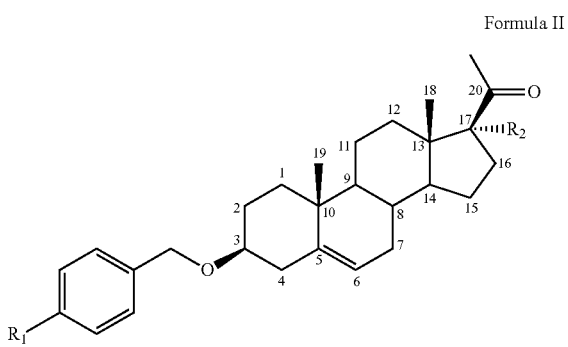

Formula II wherein:
R1 is:
C1-8 alkyl,
C1-8 alkoxy,
CN,
$NO_2$,
amino,
COOH,
$COOCH_3$,
OH,
$N_3$,
or
halogen
and
R2 is:
H,
OH,
C1-8 alkyl,
C1-8 alkoxy,
C2-C6 alkenyl,
halogen,
Bn-O—
Bn- optionally substituted with C1-8 alkyl, C1-8 alkoxy, CN, $NO_2$, amino, COOH or halogen
or
Ph- optionally substituted with C1-8 alkyl, C1-8 alkoxy, CN, $NO_2$, amino, COOH or halogen.

In a preferred embodiment, R1 is OH, C1-8 alkyl, C1-8 alkoxy or halogen, more preferably R1 is OH, methyl, ethyl, methoxy, ethoxy, methylcarboxy, Cl, Br, F or cyano.
In a preferred embodiment, R2 is H, OH, C1-8 alkyl, C1-8 alkoxy, C1-8 alkenyl or Bn, more preferably R2 is H, OH, methyl, ethyl, methoxy, ethoxy, allyl or Bn.

More preferably, the compound of the invention is:
3-(p-hydroxybenzyloxy)-pregnenolone,
3-(p-methylbenzyloxy)-pregnenolone,
3-(p-ethylbenzyloxy)-pregnenolone,
3-(p-methoxybenzyloxy)-pregnenolone,
3-(p-ethoxybenzyloxy)-pregnenolone,
3-(p-methylcarboxybenzyloxy)-pregnenolone,
3-(p-fluorobenzyloxy)-pregnenolone,
3-(p-chlorobenzyloxy)-pregnenolone,
3-(p-bromobenzyloxy)-pregnenolone,
3-(p-cyanobenzyloxy)-pregnenolone,
17-hydroxy-3-(p-hydroxybenzyloxy)-pregnenolone,
17-hydroxy-3-(p-methylbenzyloxy)-pregnenolone,
3-(p-ethylbenzyloxy)-17-hydroxy-pregnenolone,
17-hydroxy-3-(p-methoxybenzyloxy)-pregnenolone,
3-(p-ethoxybenzyloxy)-17-hydroxy-pregnenolone,
17-hydroxy-3-(p-methylcarboxybenzyloxy)-pregnenolone,
3-(p-fluorobenzyloxy)-17-hydroxy-pregnenolone,
3-(p-chlorobenzyloxy)-17-hydroxy-pregnenolone,
3-(p-bromobenzyloxy)-17-hydroxy-pregnenolone,
3-(p-cyanobenzyloxy)-17-hydroxy-pregnenolone,
3-(p-hydroxybenzyloxy)-17-methyl-pregnenolone,
17-methyl-3-(p-methylbenzyloxy)-pregnenolone,
3-(p-ethylbenzyloxy)-17-methyl-pregnenolone,
3-(p-methoxybenzyloxy)-17-methyl-pregnenolone,
3-(p-ethoxybenzyloxy)-17-methyl-pregnenolone,
17-methyl-3-(p-methylcarboxybenzyloxy)-pregnenolone,
3-(p-fluorobenzyloxy)-17-methyl-pregnenolone,
3-(p-chlorobenzyloxy)-17-methyl-pregnenolone,
3-(p-bromobenzyloxy)-17-methyl-pregnenolone,
3-(p-cyanobenzyloxy)-17-methyl-pregnenolone,
17-ethyl-3-(p-hydroxybenzyloxy)-pregnenolone,
17-ethyl-3-(p-methylbenzyloxy)-pregnenolone,
17-ethyl-3-(p-ethylbenzyloxy)-pregnenolone,
17-ethyl-3-(p-methoxybenzyloxy)-pregnenolone,
3-(p-ethoxybenzyloxy)-17-ethyl-pregnenolone,
17-ethyl-3-(p-methylcarboxybenzyloxy)-pregnenolone,
17-ethyl-3-(p-fluorobenzyloxy)-pregnenolone,
3-(p-chlorobenzyloxy)-17-ethyl-pregnenolone,
3-(p-bromobenzyloxy)-17-ethyl-pregnenolone,
3-(p-cyanobenzyloxy)-17-ethyl-pregnenolone,
3-(p-hydroxybenzyloxy)-17-methoxy-pregnenolone,
17-methoxy-3-(p-methylbenzyloxy)-pregnenolone,
3-(p-ethylbenzyloxy)-17-methoxy-pregnenolone,
17-methoxy-3-(p-methoxybenzyloxy)-pregnenolone,
3-(p-ethoxybenzyloxy)-17-methoxy-pregnenolone,
17-methoxy-3-(p-methylcarboxybenzyloxy)-pregnenolone,
3-(p-fluorobenzyloxy)-17-methoxy-pregnenolone,
3-(p-chlorobenzyloxy)-17-methoxy-pregnenolone,
3-(p-bromobenzyloxy)-17-methoxy-pregnenolone,
3-(p-cyanobenzyloxy)-17-methoxy-pregnenolone,
17-ethoxy-3-(p-hydroxybenzyloxy)-pregnenolone,
17-ethoxy-3-(p-methylbenzyloxy)-pregnenolone,
17-ethoxy-3-(p-ethylbenzyloxy)-pregnenolone,
17-ethoxy-3-(p-methoxybenzyloxy)-pregnenolone,
17-ethoxy-3-(p-ethoxybenzyloxy)-pregnenolone,
17-ethoxy-3-(p-methylcarboxybenzyloxy)-pregnenolone,
17-ethoxy-3-(p-fluorobenzyloxy)-pregnenolone,
3-(p-chlorobenzyloxy)-17-ethoxy-pregnenolone,
3-(p-bromobenzyloxy)-17-ethoxy-pregnenolone,
3-(p-cyanobenzyloxy)-17-ethoxy-pregnenolone,
17-allyl-3-(p-hydroxybenzyloxy)-pregnenolone,
17-allyl-3-(p-methylbenzyloxy)-pregnenolone,
17-allyl-3-(p-ethylbenzyloxy)-pregnenolone,
17-allyl-3-(p-methoxybenzyloxy)-pregnenolone,
17-allyl-3-(p-ethoxybenzyloxy)-pregnenolone,
17-allyl-3-(p-methylcarboxybenzyloxy)-pregnenolone, 17-allyl-3-(p-fluorobenzyloxy)-pregnenolone,
17-allyl-3-(p-chlorobenzyloxy)-pregnenolone,
17-allyl-3-(p-bromobenzyloxy)-pregnenolone,
17-allyl-3-(p-cyanobenzyloxy)-pregnenolone,
17-benzyl-3-(m-hydroxybenzyloxy)-pregnenolone,
17-benzyl-3-(p-methylbenzyloxy)-pregnenolone,
17-benzyl-3-(p-ethylbenzyloxy)-pregnenolone,
17-benzyl-3-(p-methoxybenzyloxy)-pregnenolone,
17-benzyl-3-(p-ethoxybenzyloxy)-pregnenolone,
17-benzyl-3-(p-methylcarboxybenzyloxy)-pregnenolone,
17-benzyl-3-(p-fluorobenzyloxy)-pregnenolone
17-benzyl-3-(p-chlorobenzyloxy)-pregnenolone
17-benzyl-3-(p-bromobenzyloxy)-pregnenolone or
17-benzyl-3-(p-cyanobenzyloxy)-pregnenolone.

The preferred compounds of the invention is selected from the group consisting of 3β-(p-Methoxybenzyloxy)-17α-methyl-pregnenolone, 17-benzyl-3-(p-methoxybenzyloxy)-pregnenolone, 3-(p-methoxybenzyloxy)-pregnenolone, 3-(m-bromobenzyloxy)-pregnenolone, 3-(p-methylcarboxybenzyloxy)-pregnenolone, 3-(p-methylbenzyloxy)-pregnenolone, 3-(p-fluorobenzyloxy)-pregnenolone and 3-(p-cyanobenzyloxy)-pregnenolone.

The preferred compound of the invention is 3β-(p-Methoxybenzyloxy)-17α-methyl-pregnenolone.

The invention also relates to a pharmaceutical composition comprising a compound of the invention or a pharmaceutically salt thereof and a pharmaceutically acceptable carrier.

Process for the Manufacture

The present invention also relates to a process for the manufacture of the compounds of the invention, which comprises reacting a compound of Formula III:

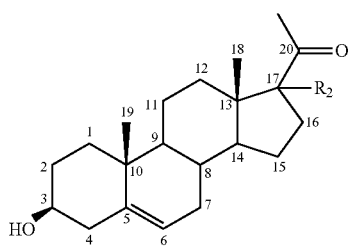

Formula III wherein R2 is as defined above,
with a compound of Formula IV:

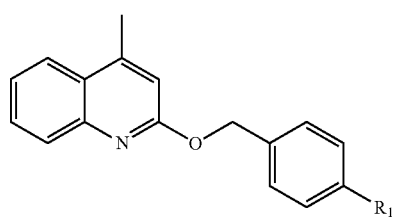

Formula IV wherein R1 is as defined above,
in the presence of a heterogeneous acid scavenger and of methyl triflate or
with a compound of Formula V

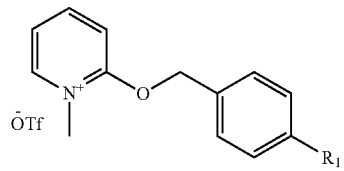

Formula V wherein R1 is as defined above
in the presence of a heterogeneous acid scavenger.

In case of a compound of formula V, there is no need for the presence of methyl triflate due to the OTf group.

In one embodiment, the process for the manufacture of the compounds of the invention, comprises reacting a compound of Formula III:

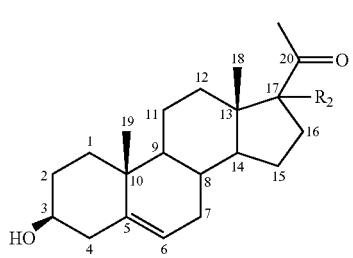

Formula III wherein R2 is as defined above,
with a compound of Formula IV:

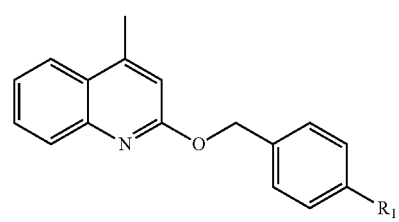

Formula IV wherein R1 is as defined above,
in the presence of a heterogeneous acid scavenger and of methyl triflate.

In another embodiment, the process for the manufacture of the compounds of the invention, comprises reacting a compound of Formula III:

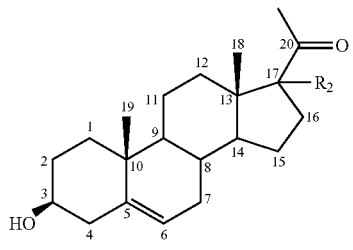

Formula III wherein R2 is as defined above, with a compound of Formula V

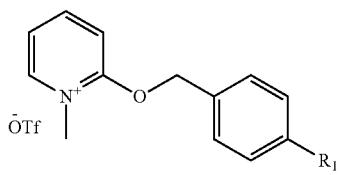

Formula V wherein R1 is as defined above
in the presence of a heterogeneous acid scavenger.

Preferably, the solvent for this reaction is an aromatic solvent such as trifluorotoluene or toluene.

Preferably, the heterogeneous acid scavenger is potassium carbonate or magnesium oxide.

Method for synthesis of compounds of formula III are well described in the prior art (Glazier E. R., 1962, Marshall et al., 1948, Jones et al., 1965).

For example, synthesis of a compound of formula III wherein R2 is an alkyl, -allyl, -benzyl or -aryl may be done by reacting pregnenolone with $Ac_2O$ to form a enol acetate. Then, the enol acetate is reacted with a Grignard reagent to generate an enolate which is subsequently trapped with a halogeno-R2.

Further, for example, synthesis of a compound of formula III wherein R2 is an alkoxy, benzyloxy or aryloxy may be is done by reacting pregnenolone with the corresponding alcohol in the presence of $Cu^{2+}$.

Method of Treatment

The present invention also relates to a compound of the invention as defined above or a pharmaceutically acceptable salt thereof for use in a method for treatment of the human or animal body.

The present invention also relates to a method for the treatment of a pathologic condition or disorder in a subject in need thereof comprising administering to said subject an effective amount of a compound of the invention as defined above or a pharmaceutically acceptable salt thereof.

The pathologies that may be treated with the compounds of the invention are those which may be treated by Pregnenolone, for example the pathologies that may be treated by Pregnenolone because of it action as an inhibitor of the CB1 receptor.

Examples of such pathologies are psychiatric and neurological disorders; neurodegenerative disorders; metabolic disorders; addiction, dependence, abuse relapse and related disorders; bladder and gastrointestinal disorders; hepatic diseases such as steatosis; non-alcoholic steatohepatitis (NASH), liver cirrhosis; alcoholic steatosis; inflammatory diseases; cardiovascular diseases; nephropathies; glaucoma; spasticity; cancer; osteoporosis; obesity; autoimmune hepatitis and encephalitis; pain or reproductive disorders and skin inflammatory and fibrotic diseases.

The present invention also relates to the use of compounds of the invention or a pharmaceutically acceptable salt thereof for the preparation of a medicament for treating one of the above mentioned pathologies.

The invention will be further illustrated by the following figures and examples. However, these examples and figures should not be interpreted in any way as limiting the scope of the present invention.

EXAMPLES

A. Examples of Synthesis of Pregnenolone Derivatives

Pregnenolone is a well-known and commercially available steroid (CAS number 145-13-1).

As shown below, Pregnenolone can be used as precursor for the synthesis of its derivatives.

1. Synthesis of Pregnenolone Derivatives Substituted in C17

First, Pregnenolone is substituted in C17.

Example of Synthesis of a Pregnenolone Derivative Having C17 Substituted with R As shown below, to synthesize a Pregnenolone substituted with an alkyl, an allyl or an aryl at C17 position, in a first step, the corresponding enol acetate is formed by reacting Pregnenolone with $Ac_2O$. Then, the enol acetate is reacted with a Grignard reagent such as MeMgBr in THF to generate an enolate which is subsequently trapped with an electrophile. The electrophile would be preferentially an R-iodo- or R-bromo wherein R is an alkyl, -allyl, -benzyl or -aryl.

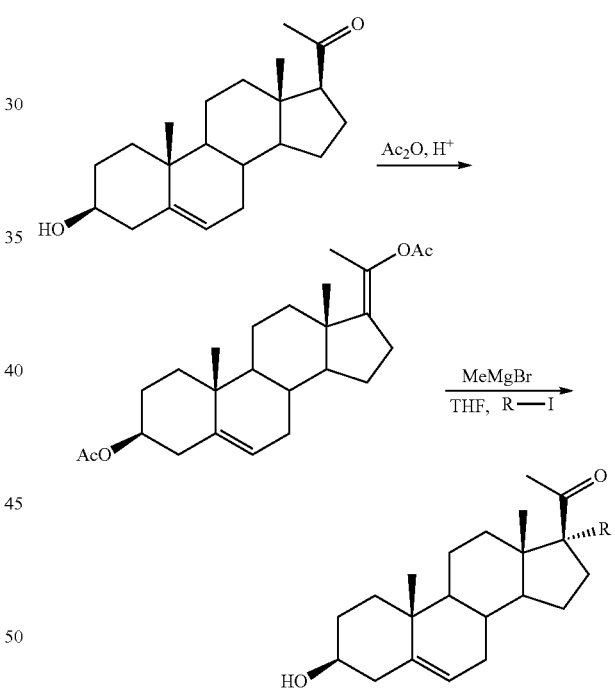

Example of Synthesis of the Enol Acetate Intermediate

As shown below, p-toluenesulfonic acid monohydrate (1.12 g; 5.9 mmol; 0.93 eq.) was added to a solution of Pregnenolone (2 g; 6.3 mmol; 1 eq.) in acetic anhydride (230 ml). The reaction medium was stirred for 5 h at reflux and acetic anhydride was slowly distilled. After allowed to cool to 20° C., the reaction medium was poured into crushed ice then the mixture is extracted with diethyl ether. The organic layer was washed with saturated aqueous $Na_2CO_3$, dried over $Na_2SO_4$ then evaporated under reduced pressure. The residue was purified by chromatography on silica gel (eluent: cyclohexane/AcOEt from 100/0 to 90/10) to give the Pregnenolone enol acetate (2.2 g; 85%) as a white solid.

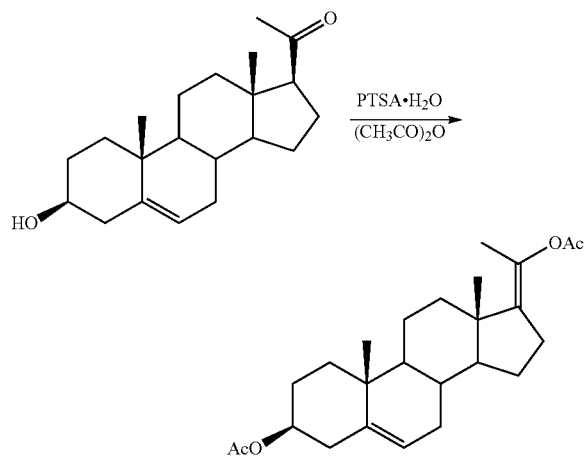

Example of Synthesis of the 17α-methyl-pregnenolone

As shown below, MeMgBr$_2$ (3M in Et$_2$O; 25 ml; 75 mmol; 10 eq.) was added to a solution of pregnenolone enol acetate (3 g; 7.5 mmol; 1 eq.) in anhydrous THF (65 ml). The reaction medium was stirred for 1 h at reflux, then allowed to cool to 20° C. CH$_3$I (4.6 ml; 75 mmol; 10 eq.) was added and reaction medium was stirred at reflux. Adding CH$_3$I was repeated every 45 minutes until 40 equivalents. After cooling to 20° C., an aqueous solution of NH$_4$Cl is added then the mixture is extracted with ethyl acetate. The organic layer was washed with brine, dried over Na$_2$SO$_4$ then evaporated under reduced pressure. The residue was purified by chromatography on silica gel (eluent: cyclohexane/AcOEt 75/25) to give the 17α-methyl-pregnenolone (600 mg; 25%) as a white solid.

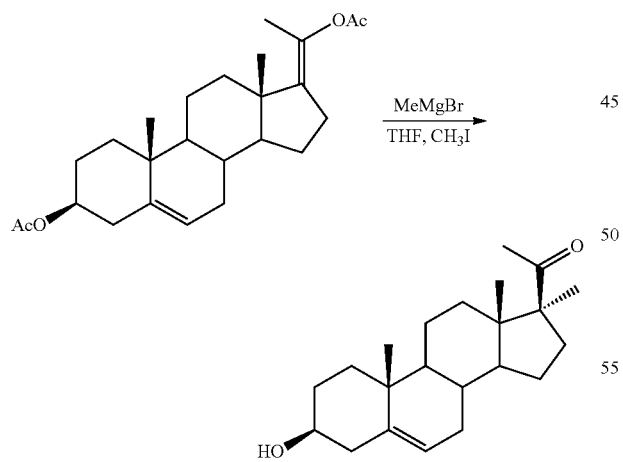

Example of Synthesis of a Pregnenolone Derivative Having C17 Substituted with —OR To synthesize a Pregnenolone substituted with an alkoxy-, benzyloxy- or aryloxy- at C17 position, Pregnenolone is reacted with the corresponding alcohol, R—OH, in the presence of Cu$^{2+}$.

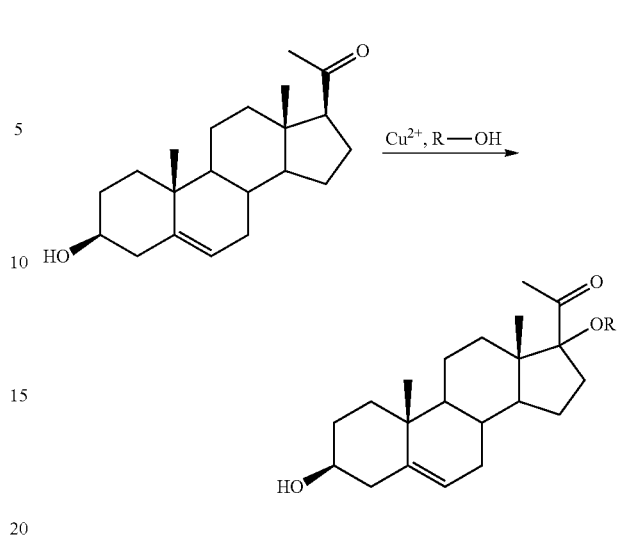

Example of Synthesis of 17-methoxy-pregnenolone

As shown below, CuBr$_2$ (4.05 g; 18.13 mmol; 1.9 eq.) was added to a suspension of pregnenolone (3 g; 9.48 mmol; 1 eq.) in methanol (360 ml). The reaction medium was stirred for 24 h at reflux, then evaporated under reduced pressure. The residue was dissolved in dichloromethane and water. The organic layer was washed with brine, dried over Na$_2$SO$_4$ then concentrated under reduced pressure. The residue was purified by chromatography on silica gel (eluent: cyclohexane/AcOEt 80/20) then by recrystallisation (acetone) to give the 17-methoxy-pregnenolone (510 mg; 15%) as a white solid.

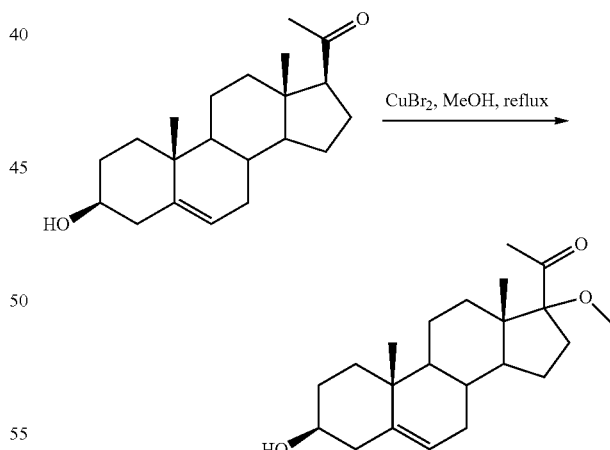

2. Synthesis of Compound of Formula IV

Some compounds of formula IV may be commercially available for example 2-(4-methoxybenzyloxy)-4-methylquinoleine.

Compounds of formula IV may also be synthetized by reacting 2-chloro-4-methylquinoleine and para-substituted benzyl alcohol in the presence of 18-crown-6 and KOH according the schema below.

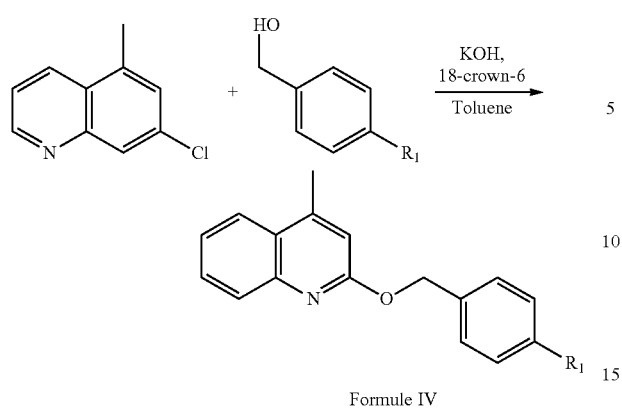

Formule IV

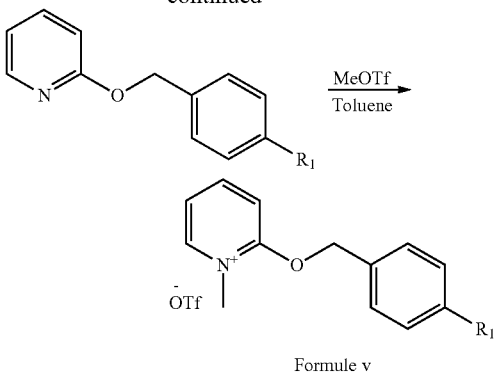

Formule v

Example of Synthesis of 2-(p-Methylbenzyloxy)-4-Methylquinoline

As shown below, to a solution of 2-chloro-4-methylquinoleine- (500 mg; 2.8 mmol; 1 eq.) in anhydrous toluene (10 mL) was added successively 4-methylbenzyl alcohol (409 mg, 3.35 mmol; 1.25 eq), KOH (630 mg; 11.2 mmol; 4.0 eq.), then 18-crown-6 (45 mg, 0.16 mmol, 0.06 eq). The reaction medium was heated at reflux for 1.5 h using a Dean-Stark trap. The reaction medium was then cooled to room temperature then water was added and product is extracted with AcOEt. The organic phase is dried ($Na_2SO_4$) then evaporated under vacuum. The residue was purified by chromatography on silica gel (eluent: cyclohexane/AcOEt 95/5) to give 2-(p-methylbenzyloxy)-4-methylquinoline (660 mg; 89%) as a colorless oil.

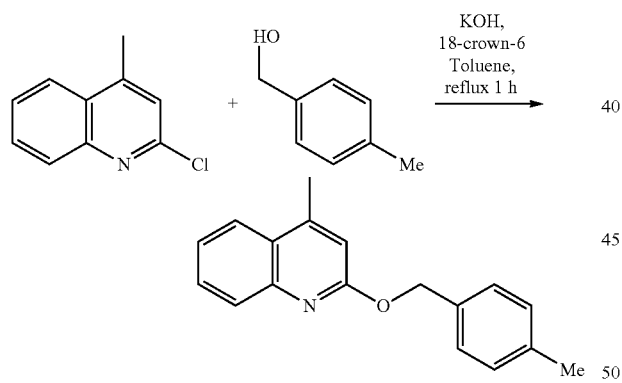

3. Synthesis of Compounds of Formula V

Compounds of formula V may be synthetized in two steps: First by reacting 2-chloropyridine and para-substituted benzyl alcohol in the presence of 18-crown-6 and KOH or t-BuOK; Second by reacting the resulting product with methyl triflate to allow the salt formation according to the schema below.

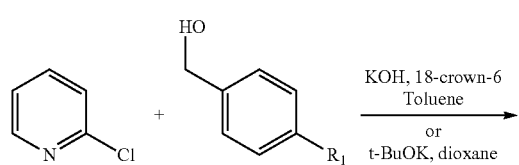

Example of Synthesis of 2-(p-bromobenzyloxy)-1-methylpyridinium triflate

As shown below, to a solution of 2-chloropyridine (0.9 mL; 9.6 mmol; 1.2 eq.) in anhydrous toluene (16 mL) was added successively 4-Bromobenzyl alcohol (1.5 g, 8.0 mmol; 1 eq), KOH (1.35 g; 24 mmol; 3.0 eq.), then 18-crown-6 (105 mg, 0.4 mmol, 0.05 eq). The reaction medium was stirred at reflux for 1 h using a Dean-Stark trap. The reaction medium was cooled to room temperature then water was added and product was extracted with AcOEt. The organic phase is dried ($Na_2SO_4$) then evaporated under vacuum. The residue was purified by chromatography on silica gel (eluent: cyclohexane/AcOEt 9/1) to give 2-(p-Bromobenzyloxy)-pyridine (2 g; 78%) as a colorless oil.

For the second step, methyl triflate, MeOTf, (450 µL; 3.97 mmol; 1.05 eq) was added to a cold solution of 2-(p-bromobenzyloxy)-pyridine (1 g; 0.3.7 mmol; 1 eq). The reaction medium was stirred for 2 hours at room temperature then evaporated under vacuum to give quantitatively 2-(p-Bromobenzyloxy)-1-methylpyridinium Triflate (1.6 g) as a white solid.

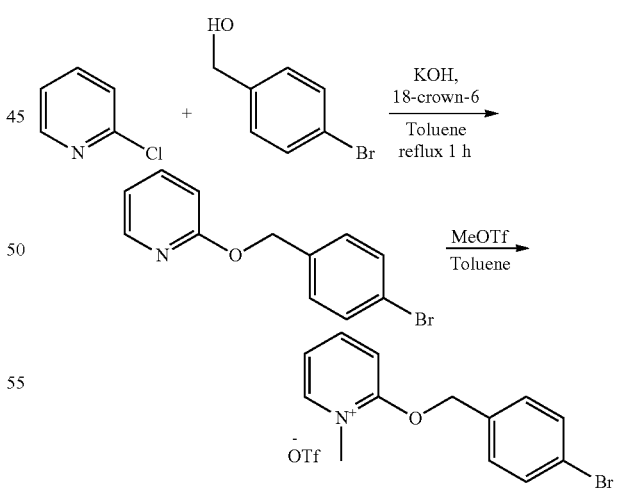

Example of Synthesis of 2-(p-Methylcarboxybenzyloxy)-1-methylpyridinium Triflate As shown below, to a solution of 2-chloropyridine (1.13 mL; 12.0 mmol; 1.0 eq.) in anhydrous dioxane (48 mL) was added successively 4-Methylcarboxy-benzyl alcohol (1.5 g, 8.0 mmol; 1 eq) and t-BuOK (2 g; 18 mmol; 1.5 eq.). The reaction medium was heated at reflux for 16 h. The reaction medium was cooled to room temperature then water was added and product is extracted with AcOEt. The organic phase is dried (Na$_2$SO$_4$) then evaporated under vacuum. The residue was purified by chromatography on silica gel (eluent: cyclohexane/AcOEt 96/4) to give 2-(p-Methylcarboxybenzyloxy)-pyridine (1.13 g; 39%) as a colorless oil.

For the second step, MeOTf, (293 μL; 2.59 mmol; 1.05 eq) was added to a cold solution of 2-(p-Methylcarboxybenzyloxy)-pyridine (600 mg; 2.46 mmol; 1 eq). The reaction medium was stirred for 2 hours at room temperature then evaporated under vacuum to give quantitatively 2-(p-Methylcarboxybenzyloxy)-1-methylpyridinium Triflate (0.9 g) as a white solid.

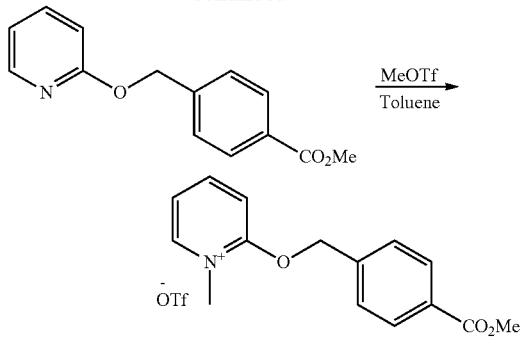

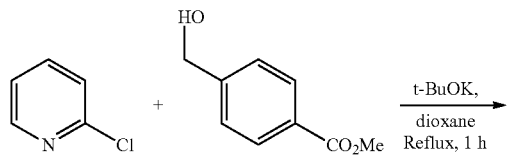

4. Synthesis of Pregnenolone Derivatives Having C3 Substituted with Para-Substituted Benzyloxy Starting from Pregnenolone or Pregnenolone derivative having the suitable group in C17, the pregnenolone or pregnenolone derivative is substituted in C3 with a group OBn-R1 according to known methods of benzylation of alcohol (Poon K W C. et al. 2006, Giannis et al., 2009, Nwoye, E. O et al., 2007) and as shown below.

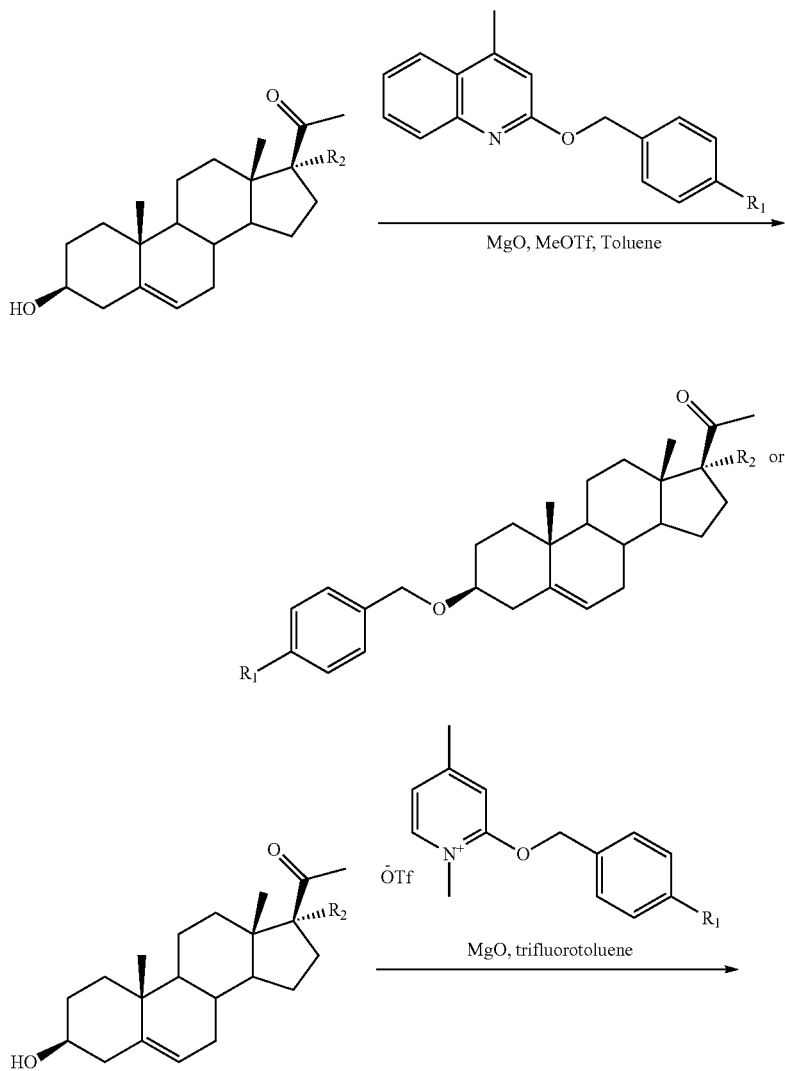

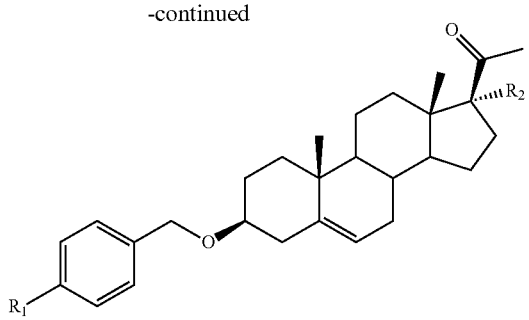

Example of Benzylation of Pregnenolone

As shown below, MgO (46 mg; 1.14 mmol; 2 eq.) and 2-benzyloxy-1-methylpyridinium triflate (400 mg; 1.14 mmol; 2.0 eq.) were added to a solution of pregnenolone (181 mg; 0.57 mmol; 1 eq.) in trifluorotoluene (4 ml). The reaction medium was stirred for one night at 85° C., then filtered on celite and evaporated under reduced pressure. The residue was purified by chromatography on silica gel (eluent: cyclohexane/AcOEt 95/5) to give the 3β-benzyloxy-pregnenolone (0.16 g; 70%) as a white solid.

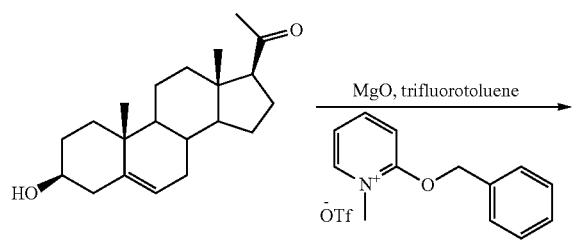

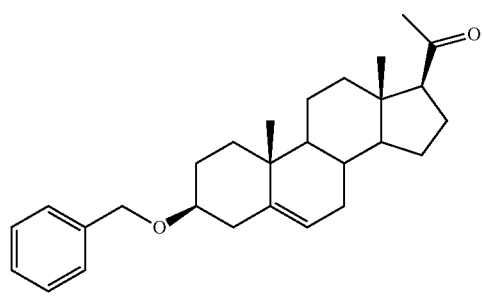

Example of benzylation of 17α-benzylpregnenolone

As shown below, MgO (116 mg; 2.42 mmol; 2.0 eq.) and 2-benzyloxymethylpyridinium triflate (1 g; 2.86 mmol; 2.0 eq.) were added to a solution of 17α-benzylpregnenolone (580 mg; 1.43 mmol; 1 eq.) in trifluorotoluene (15 ml). The reaction medium was stirred for one night at 85° C., then filtered on celite and evaporated under reduced pressure. The residue was purified by chromatography on silica gel (eluent: cyclohexane/AcOEt 95/5) to give the 3β-benzyloxy-17α-benzyl-pregnenolone (300 mg; 42%) as a white solid.

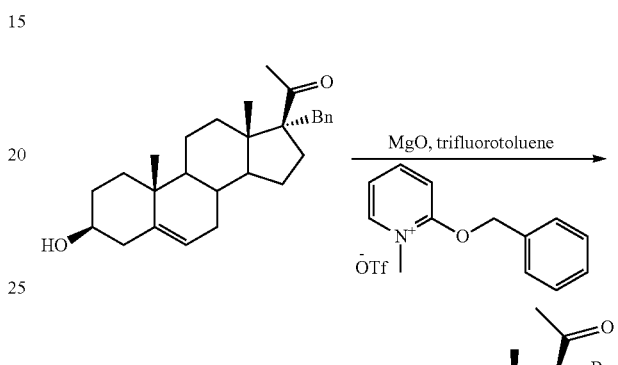

Example of Synthesis of the 3β-(p-bromobenzyloxy)-pregnenolone

A shown below, to a solution of pregnenolone (477 mg; 1.51 mmol; 1 eq.) in anhydrous α,α,α-trifluorotoluene (9 mL) was added MgO (121 mg; 3.02 mmol; 2.0 eq.) then 2-(p-Bromobenzyloxy)-1-methylpyridinium Triflate (1.29 g; 3.02 mmol; 2.0 eq.). The reaction medium was stirred for 20 h at 100° C., and then filtered on celite. Water was added and product is extracted with AcOEt. The organic phase is dried (Na$_2$SO$_4$) then evaporated under vacuum. The residue was purified by chromatography on silica gel (eluent: cyclohexane/AcOEt 96/4) then triturated with acetone to give the 3β-(p-bromobenzyloxy)-pregnenolone (375 mg; 49%) as a white solid.

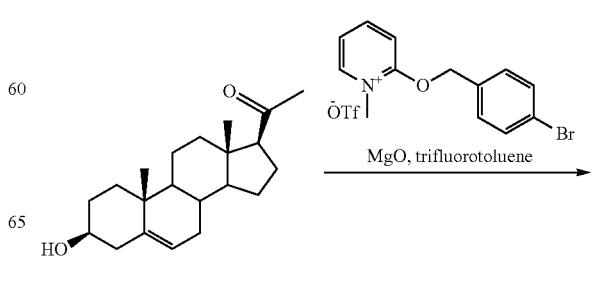

-continued

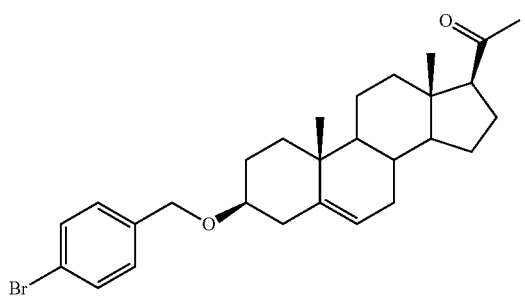

Example of Synthesis of 3β-(p-Methoxybenzyloxy)-pregnenolone

As shown below, to a solution of pregnenolone (250 mg; 0.79 mmol; 1 eq.) in anhydrous toluene was added successively MgO (63 mg; 1.58 mmol; 2.0 eq.), 2-(4-methoxybenzyloxy)-4-methylquinoleine (441 mg; 1.58 mmol; 2.0 eq.) and methyl triflate (MeOTf) (180 μl; 1.58 mmol; 2 eq). The reaction medium was stirred for 20 h at 60° C., and then filtered on celite. Water was added and product is extracted with AcOEt. The organic phase is dried (Na₂SO₄) then evaporated under vacuum. The residue was purified by chromatography on silica gel (eluent: cyclohexane/AcOEt 9/1) to give the 3β-(p-methoxybenzyloxy)-pregnenolone (160 mg; 43%) as a white solid.

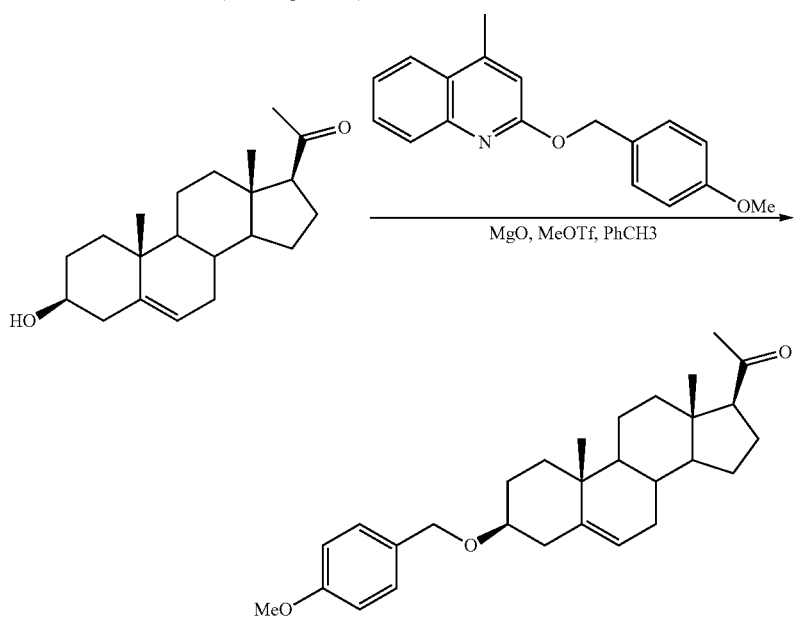

Example of Synthesis of 3β-(p-methoxybenzyloxy)-17α-methyl-pregnenolone

17α-methyl-pregnenolone was synthesized as shown above.

To a solution of 17α-methyl-pregnenolone (170 mg; 0.5 mmol; 1 eq.) in anhydrous toluene was added successively MgO (40 mg; 1 mmol; 2 eq.), 2-(4-methoxybenzyloxy)-4-methylquinoleine (290 mg; 1 mmol; 2 eq), and methyl triflate (MeOTf) (0.11 ml; 1 mmol; 2 eq). The reaction medium was stirred for one night at 85° C., and then filtered on celite. Water was added and product is extracted with AcOEt. The organic phase is dried (Na₂SO₄) then evaporated under vacuum. The residue was purified by chromatography on silica gel (eluent: cyclohexane/AcOEt from 1/0 to 95/5) then triturated with acetone to give the 3β-(p-Methoxybenzyloxy)-17α-methyl-pregnenolone (80 mg; 35%) as a white solid.

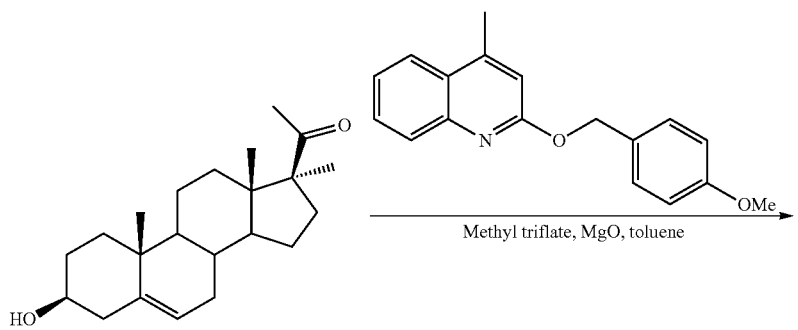

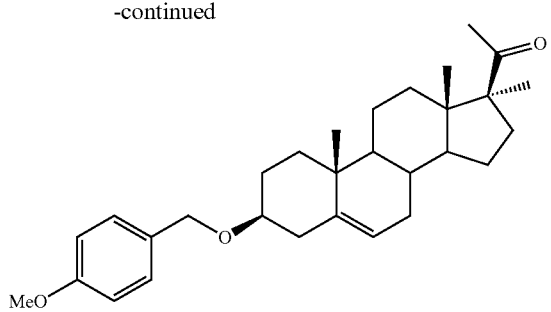

Example of Synthesis of 3β-(p-methoxybenzyloxy)-17α-benzyl-pregnenolone

17α-benzyl-pregnenolone was synthesized as shown above.

To a solution of 17α-benzyl-pregnenolone (1.9 g; 4.66 mmol; 1 eq.) in anhydrous toluene (45 ml) was added successively MgO (373 mg; 9.3 mmol; 2 eq.), 2-(4-methoxybenzyloxy)-4-methylquinoleine (2.6 g; 9.33 mmol; 2 eq), and methyl triflate (MeOTf) (1.06 ml; 9.33 mmol; 2 eq). The reaction medium was stirred for one night at 40° C., and then filtered on celite. Water was added and product is extracted with AcOEt. The organic phase is dried ($Na_2SO_4$) then evaporated under vacuum. The residue was purified by chromatography on silica gel (eluent: cyclohexane/AcOEt 9/1) then triturated with acetone to give the 3β-(p-methoxybenzyloxy)-17α-benzyl-pregnenolone (1.18 g; 49%) as a white solid.

B. Capacity of Pregnenolone Derivatives not to be Converted in Other Active Steroids Derived from Pregnenolone Material and Methods In Vitro Test of Metabolization Alternatively the compound can be administered to any cell line expressing the enzyme that metabolizes pregnenolone in culture, measuring then the content of metabolites of pregnenolone within the cell or on the cell culture medium by GC/MS and comparing these concentrations to metabolites in cell cultures that have been received only a vehicle or pregnenolone.

In this example, CHO cell line was used. These cells derived from the ovary have all the enzymes needed to metabolize pregnenolone in downstream steroids.

The content in CHO culture medium of allopregnanolone (ALLO), epiallopregnanolone (EPIALLO), pregnenolone (PREG), DHEA, and testosterone (TESTO) was measured by GC/MS.

Results:

Pregnenolone Derivatives for which the Transformation in Downstream Active Steroids In Vitro is Limited.

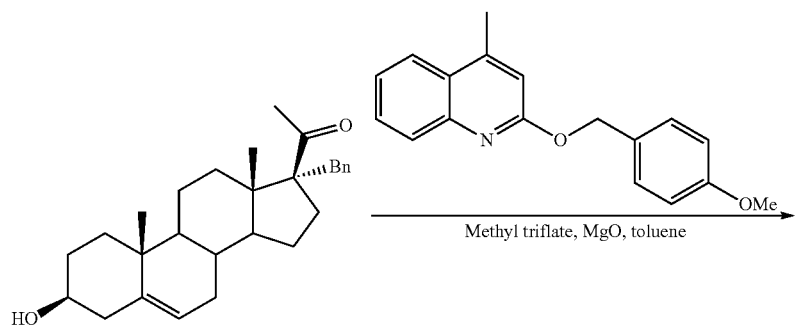

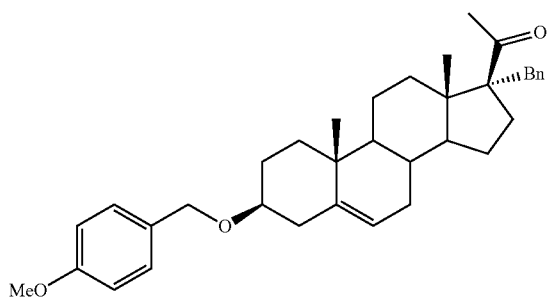

The inventors have analyzed the metabolism of pregnenolone derivatives using an in vitro test in CHO cells.

The administration of Pregnenolone (1 μM) to these cells for 48 hours produced a significant increase in Allopregnanolone and Epiallopregnanolone in the culture medium (Table 1).

TABLE 1

Table 1: Pregnenolone metabolism

|  |  | ALLO | EPIALLO | PREG | DHEA | TESTO |
|---|---|---|---|---|---|---|
| Control cell cultures | Steroid levels | 0.00 | 0.00 | 96.92 | 0.00 | 0.00 |
| Pregnenolone (1 μM) treated cells | pg/ml | 3529.99 | 16963.84 | 11440.66 | 0.00 | 0.00 |

Pregnenolone derivatives having C3 substituted with benzyloxy were tested using in vitro test in CHO cells.

Results are shown in Table 2 below. Results expressed as percentage changes from CHO cells treated with Pregnenolone or as pg/ml (0=concentrations below the detection limit).

TABLE 2

| N° | Name | Structure | % changes from Pregnenolone treated cells | | | pg/ml | |
|---|---|---|---|---|---|---|---|
|  |  |  | ALLO | EPIALLO | PREG | DHEA | TESTO |
| 42 | 3β-Benzyloxy-17α-methyl-pregnenolone | | −99.87 | −99.94 | −100.00 | 0.00 | 0.00 |
| 63 | 17α-Benzyl-3β-benzyloxy-pregnenolone | | −99.01 | −99.84 | −99.87 | 0.00 | 0.00 |
| 41 | 3β-Benzyloxy-pregnenolone | | −98.82 | −99.88 | −99.35 | 0.00 | 0.00 |

TABLE 2-continued

| | Reduced metabolin | | % changes from Pregnenolone treated cells | | | pg/ml | |
|---|---|---|---|---|---|---|---|
| N° | Name | Structure | ALLO | EPIALLO | PREG | DHEA | TESTO |
| 68 | 3β-(p-methoxy-benzyloxy)-17α-methyl-pregnenolone | | −100.00 | −100.00 | −100.00 | 0 00 | 0.00 |

As shown in table 2, the compound 68, 3β-(p-Methoxybenzyloxy)-17α-methyl-pregnenolone, is not metabolised in Pregnenolone and the compounds 63 and 41 are not significantly metabolized in Pregnenolone (metabolization <1%).

Pregnenolone derivatives that contain a 3-benzyloxy function (substituted or not) show no detectable metabolization of derivative of Pregnenolone in DHEA and Testosterone and very low metabolization in Allopregnanolone and Epiallopregnanolone.

These results show the presence of a OBn-R group in C3 avoid the conversion of Pregnenolone derivatives into Pregnenolone and Pregnenolone metabolites, in particular metabolites whose Pregnenolone is precursor and that are endowed with progestative, androgenic, estrogenic, glucocorticoid activity, or neuromodulatory properties.

REFERENCES

Throughout this application, various references describe the state of the art to which this invention pertains. The disclosures of these references are hereby incorporated by reference into the present disclosure.

Aird R B. The effect of desoxycorticosterone in epilepsy. The Journal of Nervous and Mental Disorders. 1944; 99:501-510.

Aird R B, Gordan G S. Anticonvulsive properties of desoxycorticosterone. Journal of the American Medical Association. 1951; 145:715-719

Baulieu E E (1991) Neurosteroids: A new function in the brain. Biol Cell 71:3-10.

Falkenstein E, Tillmann H C, Christ M, Feuring M and Wehling M. Multiple actions of steroid hormones—a focus on rapid, nongenomic effects. Pharmacol Rev. 2000 December; 52(4):513-56.

García-Estrada J, Luquín S, Fernández A M, Garcia-Segura L M. Dehydroepiandrosterone, pregnenolone and sex steroids down-regulate reactive astroglia in the male rat brain after a penetrating brain injury. Int J Dev Neurosci. 1999 April; 17(2):145-51.

Gasior M, Carter R B, Witkin J M. Neuroactive steroids: potential therapeutic use in neurological and psychiatric disorders. Trends Pharmacol Sci. 1999 March; 20(3):107-12. Review.

Giannis A., Heretsch P., Sarli V. and Stöβel A., Synthesis of Cyclopamine Using a Biomimetic and Diastereoselective Approach. Angew Chem Int Ed Engl. 2009, 48(42), 7911-7914.

Glazier, E. R. Bromination with Cupric Bromide. II.1,2 Bromination in the Presence of an Olefinic Bond; J. Org. Chem. 1962, 27, 4397-4399.

Gursoy E, Cardounel A, Kalimi M. Pregnenolone protects mouse hippocampal (HT-22) cells against glutamate and amyloid beta protein toxicity. Neurochem Res. 2001 January; 26(1):15-21.

Green C J, Halsey M J, Precious S, Wardley-Smith B. Alphaxolone-alphadolone anesthesia in laboratory animals. Laboratory Animals. 1978; 12:85-89.

Gyermek L, Genther G, Fleming N. Some effects of progesterone and related steroids on the central nervous system. International Journal of Neuropharmacology. 1967; 6:191-198.

Jones E. R. H. and Wilson D. A., Studies in the steroid group. Part LXXVI. The methylation of enol acetates and bromo-ketones. Nuclear magnetic resonance spectra of 11-keto-steroids. J. Chem. Soc., 1965, 2933-2944.

Lambert J J, Belelli D, Peden D R, Vardy A W, Peters J A. Neurosteroid modulation of GABAA receptors. Progress in Neurobiology. 2003; 71:67-80.

Majewska M D, Harrison N L, Schwartz R D, Barker J L and Paul S M Steroid hormone metabolites are barbiturate-like modulators of the GABA receptor. Science (Wash D.C.) (1986) 232:1004-1007.

Marshall C. W., Kritchevsky T. H., Lieberman S., and Gallagher T. F. Preparation of 17-Ketosteroids from Enol Acetates of 20-Ketosteroids. J. Am. Chem. Soc., 1948, 70 (5), pp 1837-1839

Mathis C, Paul S M, Crawley J N. The neurosteroid pregnenolone sulfate blocks NMDA antagonist-induced deficits in a passive avoidance memory task. Psychopharmacology (Berl). 1994 October; 116(2):201-6.

Nwoye, E. O. and Dudley, G. B. A method for the synthesis of para-methoxybenzyl (PMB) ethers under effectively neutral conditions. Chem. Commun. 2007, 1436-1437.

Paul S M, Purdy R H. Neuroactive steroids FASEB J. 1992 March; 6(6):2311-22. Review.

Poon K W C. and Dudley G. B., Mix-and-Heat Benzylation of Alcohols Using a Bench-Stable Pyridinium Salt J. Org. Chem., 2006, 71, 3923-3927

Reddy D S, Rogawski M A. Enhanced anticonvulsant activity of ganaxolone after neurosteroid withdrawal in a rat model of catamenial epilepsy. Journal of Pharmacology and Experimental Therapeutics. 2000a; 294:909-915.

Reddy D S. Pharmacology of endogenous neuroactive steroids. Critical Reviews in Neurobiology. 2003; 15:197-234.

Reddy D S. Mass spectrometric quantification and physiological-pharmacological activity of androgenic neurosteroids. Neurochemistry International. 2008; 52(4-5):541-553.

Reddy D S. Neurosteroids: endogenous role in the human brain and therapeutic potentials. Prog Brain Res. 2010; 186:113-37. Review.

Rupprecht R. The neuropsychopharmacological potential of neuroactive steroids. J Psychiatr Res. 1997 May-June; 31(3):297-314. Review.

Vallée M., Vitiello S., Bellocchio L., Hebert-Chatelain E., Monlezun S., Martin-Garcia E., Kasanetz F., Baillie G. L., Panin F., Cathala A., Roullot-Lacarrière V., Fabre S., Hurst D. P., Lynch D. L., Shore D. M., Deroche-Gamonet V., Spampinato U., Revest J. M., Maldonado R., Reggio P. H., Ross R. A., Marsicano G. and Piazza P. V. Pregnenolone can protect the brain from cannabis intoxication. Sciences. 2013. In press

The invention claimed is:

1. A compound of Formula I or a pharmaceutically acceptable salt thereof,

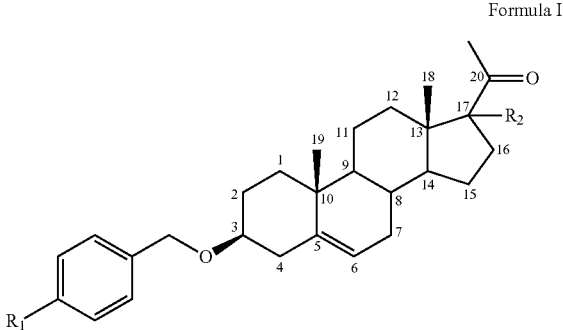

Formula I wherein:
R1 is methoxy and
R2 is H.

2. The compound according to claim 1 wherein R2 is in α position.

3. A pharmaceutical composition comprising a compound according to claim 1 or a pharmaceutically acceptable salt thereof and a pharmaceutically acceptable carrier.

4. A pharmaceutical composition comprising a compound according to claim 2 or a pharmaceutically acceptable salt thereof and a pharmaceutically acceptable carrier.

* * * * *